(12) United States Patent
Piron et al.

(10) Patent No.: US 11,992,304 B2
(45) Date of Patent: May 28, 2024

(54) MAGNETIC RESONANCE IMAGING SYSTEM AND METHODS FOR USE WITH A MEDICAL ROBOTIC SYSTEM

(71) Applicant: SYNAPTIVE MEDICAL INC., Toronto (CA)

(72) Inventors: Cameron Anthony Piron, Toronto (CA); Alexander Gyles Panther, Toronto (CA); Thanh Vinh Vuong, Kitchener (CA); Diana Lee, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 381 days.

(21) Appl. No.: 17/014,640

(22) Filed: Sep. 8, 2020

(65) Prior Publication Data
US 2021/0068701 A1   Mar. 11, 2021

Related U.S. Application Data

(60) Provisional application No. 62/896,877, filed on Sep. 6, 2019.

(51) Int. Cl.
*A61B 5/055* (2006.01)
*A61B 34/30* (2016.01)
*A61B 90/00* (2016.01)
*G01R 33/28* (2006.01)
*G01R 33/563* (2006.01)

(52) U.S. Cl.
CPC .............. *A61B 5/055* (2013.01); *A61B 34/30* (2016.02); *A61B 90/37* (2016.02); *G01R 33/285* (2013.01); *G01R 33/56341* (2013.01); *G01R 33/5635* (2013.01); *A61B 2090/3735* (2016.02); *A61B 2090/374* (2016.02); *A61B 2090/3764* (2016.02); *A61B 2090/378* (2016.02)

(58) Field of Classification Search
CPC ......... A61B 5/055; A61B 90/30; A61B 34/00; A61B 34/30
See application file for complete search history.

(56) References Cited

U.S. PATENT DOCUMENTS 8,812,077 B2 * 8/2014 Dempsey ............. A61N 5/1049
600/410
10,478,253 B2 * 11/2019 Mak .................... G01B 9/02091
10,775,454 B2 * 9/2020 Poole ................. G01R 33/3858
(Continued)

OTHER PUBLICATIONS

Eckhard Hempel, An MRI-Compatible Surgical Robot for Precise Radiological Intervention, Computer Aided Surgery (Year: 2003).*
(Continued)

*Primary Examiner* — Serkan Akar
*Assistant Examiner* — Mark Louis Alyass

(57) ABSTRACT

A magnetic resonance imaging (MRI) system and methods for use with a medical, e.g., a surgical, robotic system, involving an MRI apparatus configured to operate with the surgical robotic system, the MRI apparatus having at least one low-field magnet, the at least one low-field magnet configured to generate a low magnetic field, and the low magnetic field comprising a magnetic flux density in a range of approximately 0.1 Tesla (T) to approximately 0.5 T, whereby a standoff between the MRI apparatus and the surgical robotic system is reduced.

11 Claims, 8 Drawing Sheets

(56) References Cited

U.S. PATENT DOCUMENTS 10,888,386 B2 * 1/2021 Eyre ............... A61G 13/08

OTHER PUBLICATIONS

Nainesh Parikh, Practical guide for implementing hybrid PET/MR clinical service: lessons learned from our experience, Springer Science, Abdominal Imaging (Year: 2015).*

David Weingarten, Cortical mapping and frameless stereotactic navigation in the high-field intraoperative magnetic resonance imaging suite, Journal of Neurosurgery (Year: 2009).*

Asch, Diagnostic yield and accuracy of CT angiography, MR angiography, and digital subtraction angiography for detection of macrovascular causes of intracerebral haemorrhage: prospective, multicentre cohort study (Year: 2015).*

Rappard, MR-Guided Catheter Navigation of the Intracranial Subarachnoid Space, American Journal of Neuroradiology (Year: 2003 ).*

* cited by examiner

MAGNETIC RESONANCE IMAGING SYSTEM AND METHODS FOR USE WITH A MEDICAL ROBOTIC SYSTEM

CROSS-REFERENCE TO RELATED APPLICATION(S)

This document is a non-provisional patent application claiming the benefit of, and priority to, U.S. Provisional Patent Application Ser. No. 62/896,877, filed on Sep. 6, 2019, and entitled "System and method of Using a Combined MRI and Surgical Robotic System," which is hereby incorporated by reference in its entirety.

FIELD

Generally, the present disclosure relates to magnetic resonance imaging (MRI) technologies, More particularly, the present disclosure relates to MRI and robotic technologies. Even more particularly, the present disclosure relates to MRI and robotic technologies for surgical implementations.

BACKGROUND

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimes, and radiation therapy are only a few examples of procedures utilizing imaging guidance in the medical field.

Advanced imaging modalities, such as MRI, have led to improved rates and accuracy of detection, diagnosis and staging in several fields of medicine, including neurology, wherein imaging of diseases, such as brain cancer, stroke, Intra-Cerebral Hemorrhage ("ICH"), and neurodegenerative diseases, such as Parkinson's and Alzheimer's, are performed. As an imaging modality, MRI enables three-dimensional visualization of tissue with high contrast in soft tissue without the use of ionizing radiation. MRI may be used in conjunction with other modalities, such as ultrasound (US), positron emission tomography (PET), x-ray imaging, and computerized tomography (CT), by examining the same tissue using the different physical principals associated with each modality. CT may be used to visualize honey structures; and CT may be used in conjunction with an intra-venous agent, such as an iodinated contrast agent, to visualize blood vessels. MRI may also be performed using a similar contrast agent, such as an intra-venous gadolinium-based contrast agent having pharmaco-kinetic properties, that enables visualization of tumors and break-down of the blood brain barrier. These multi-modality solutions provide varying degrees of contrast in relation to various parameters, such as tissue type, tissue function, and disease state. Imaging modalities are in either isolation or combination to better differentiate and diagnose disease.

In neurosurgery, for example, brain tumors are typically excised through an open craniotomy approach guided by imaging. The data collected in these solutions typically consists of CT scans with an associated contrast agent, such as iodinated contrast agent, as well as MRI scans with an associated contrast agent, such as gadolinium contrast agent. Also, optical imaging is often used in the form of a microscope to differentiate the boundaries of the tumor from healthy tissue, referred to as the peripheral zone. Tracking of instruments relative to the patient and the associated imaging data is also often achieved by way of external hardware systems, such as mechanical arms, radiofrequency, or optical tracking devices. As a set, these external hardware systems are referred to as surgical navigation systems.

The link between immunological response imaging and therapy is critical to managing treatment in a number of areas, such as oncology, MS lesions, stroke penumbra, traumatic brain injury, etc. Observing a natural immune response to a tumor or trauma as well as an immune response being mediated by therapy, e.g., an increased or decreased immune response as a result of tumor or brain injury therapy, is desirable. Macrophages play a key role in the immunological response; therefore, the ability to image and track macrophage activity in vivo provides insight into the immunological response of the body.

Nuclear magnetic resonance (NMR) imaging or MRI is a non-invasive imaging modality that produces high-resolution, high-contrast images of an interior of a subject. MRI involves the interrogation of the nuclear magnetic moments of a sample that is placed in a strong magnetic field with radio frequency (RF) magnetic fields. During an MRI scan, the subject, typically a human patient, is placed into the bore of an MRI machine having by a polarizing magnet and RF coils housed within; and the patient is subjected to a uniform static polarizing magnetic field $B0$ that is generated by the polarizing magnet. RF pulses are generated by RF coils in accordance with a particular localization method, wherein the RF pulses are used to scan target tissue of the patient. MRI signals are radiated by excited nuclei in the target tissue in the intervals between consecutive RF pulses and are sensed by the RF coils. During MRI signal sensing, gradient magnetic fields are switched rapidly to alter the uniform magnetic field at localized areas, thereby allowing spatial localization of MRI signals radiated by selected slices of the target tissue. The sensed MRI signals are, in turn, digitized and processed to reconstruct images of the target tissue slices.

When a substance, such as human tissue, is subjected to the static polarizing magnetic field $B0$, the individual magnetic moments of the spins in the tissue attempt to align with the static polarizing magnetic field $B0$, but process about the static polarizing magnetic field $B0$ in a random order at each characteristic Larmor frequency. The net magnetization vector lies along the direction of the static polarizing magnetic field $B0$ and is referred to as the equilibrium magnetization $M0$. In this configuration, the Z-component of the magnetization or longitudinal magnetization $MZ$ is equal to the equilibrium magnetization $M0$. If the target tissue is subjected to an excitation magnetic field $B1$ in the x-y plane and is near the Larmor frequency, the longitudinal magnetization $MZ$ may be rotated, or "tipped" into the x-y plane to produce a net transverse magnetic moment $MXY$. When the excitation magnetic field $B1$ is terminated, relaxation of the excited spins occurs, with a signal being emitted that effects the magnitude of radiated MRI signals. The emitted signal is received and processed to form an image.

In particular, when the excitation magnetic field $B1$ is terminated, the longitudinal magnetization $MZ$ returns to its equilibrium. The time constant that describes the manner in which the longitudinal magnetization $MZ$ returns to its equilibrium value is referred to as the spin lattice relaxation time $T1$. The spin lattice relaxation time $T1$ characterizes the time required to reduce the difference between the longitudinal magnetization $MZ$ and its equilibrium value $M0$ to zero. The net transverse magnetic moment $MXY$ also returns to its equilibrium when the excitation magnetic field B1 is terminated. The time constant that describes the manner in which the transverse magnetic moment MXY returns to its equilibrium value is referred to as the transverse relaxation time or spin-spin relaxation time T2. The transverse relaxation time T2 characterizes the time required to reduce the transverse magnetic moment MXY to zero. Both the spin lattice relaxation time T1 and the transverse relaxation time T2 are tissue specific and vary with concentration of different chemical substances in the tissue as well as with different microstructural features of the tissue. Variations of the spin lattice relaxation time T1 and/or the transverse relaxation time T2 from normal can also be indicative of disease or injury.

Like many diagnostic imaging modalities, MRI is to differentiate tissue types, e.g., muscles from tendons, white matter from gray matter, healthy tissue from pathologic tissue. Many different MRI techniques are used, the utility of each MRI technique dependent on a particular tissue under examination. Some MRI techniques involve examining a rate of tissue magnetization, while other MRI techniques involve measuring the amount of bound water or the velocity of blood flow in the tissue. Often, several MRI techniques are used together to improve tissue identification. In general, the greater the number of tests that are available, the better chance of producing a correct diagnosis exists.

In some instances, contrast agents are used to emphasize certain anatomical regions. For example, a gadolinium chelate is injected into a blood vessel to produce enhancement of the vascular system or the presence and distribution of leaky blood vessels. Iron-loaded stem cells are injected into the body and are detected via an MRI technique, thereby allowing tracking of in vivo stem cell migration and implantation. For a contrast agent to be effective, the contrast agent must preferentially enhance one tissue type over another tissue type or one organ type over another organ type. Furthermore, the preferential augmentation of signal must be specific to a particular tissue type or a particular cell of interest.

All contrast agents will shorten the T1 and T2 relaxation times of nearby tissue; however, subdividing the contract agents into two main groups is useful. T1 contrast agents, or "positive" agents, decrease T1 approximately the same amount as T2. The T1 contrast agents typically give rise to increases in signal intensity in images. Examples of T1 agents are paramagnetic gadolinium-based agents and manganese-based agents. The second group can be classified as T2 contrast agents, or "negative" agents. The T2 contrast agents decrease T2 much more than T1 and, hence, typically result in a reduction of signal intensity in images. Examples of T2 contrast agents are ferromagnetic-based particles and superparamagnetic-iron-oxide-based particles, referred to as superparamagnetic iron oxide (SPIO) and ultra-small superparamagnetic iron oxide (USPIO) particles.

Contrast agents can further be classified as targeted or non-targeted. A targeted contrast agent has the ability to bind to specific molecules of interest. In some cases, the T1 relaxation time of the agent significantly decreases upon binding. For example, MS-325 is an agent that binds to serum albumin in the blood. For many agents (including MS-325), the T1 relaxation time of the agent in the bound state is a strong function of the magnetic field strength. When this is the case, i.e., a molecule's T1 relaxation time is a strong function of the magnetic field strength, the molecule is said to have T1 dispersion.

One MRI technique involves delta relaxation enhanced magnetic resonance (DREMR), generally referred to as field-cycled relaxometry or field-cycled imaging, which relies on using underlying tissue contrast mechanisms that vary with the strength of the applied magnetic field in order to generate image contrasts. To achieve DREMR contrast, the main magnetic field is varied, as a function of time, during specific portions of an MR pulse sequence. A field-shifting electromagnet coil is used to perform the field variation. The DREMR technique exploits the difference in the T1 dispersion property (variation of T1 with field strength) of targeted T1 contrast agents in the bound and unbound states in order to obtain an image that contains signal only from contrast agent that is in the bound state, while suppressing signal from contrast agent in the unbound state. The T1 relaxation time of iron-oxide-based contrast agents also varies with the strength of the magnetic field, wherein such relationship can be harnessed. Therefore, the DREMR technique is used in order to obtain images from specific signals associated with regions where the iron-oxide-based contrast agents have accumulated.

Relatively recently, iron oxide nanoparticles have become the preferred approach to track macrophage activity within the body. This is achievable because macrophages have naturally high endocytosis activity and hence will "eat" or consume the contrast agent after the contrast agent has been injected into the subject. Once at least one of (a) a substantial amount of contrast agent has accumulated in at least one of the macrophage and (b) a substantial amount of macrophages containing minute amounts of contrast agent have accumulated, the signal will decrease in the immediate area due to the shortening of T2 caused by the contrast agent. This change in signal can be detected by use of subtraction between pre-injection images and post-injection images.

In the related art, the footprint of equipment in a surgical theater is growing with the number of medical equipment and medical personnel. Further, as medical equipment becomes combined, such as robotic equipment, lighting equipment, imaging equipment, display equipment, and the like, the size of their holding equipment or their transporting equipment also increases. As such, useable floorspace in an operating theater is decreasing and compromising the efficiency of performing medical procedures.

Referring to FIG. 1, this diagram illustrates the limited useable floorspace F in an operating theater, such as an operating room OR, which results in many challenges for medical personnel, in accordance with the prior art. In the operating theater, many pieces of medical equipment are typically utilized, such as a medical bed 1 having a location 1a for disposing a patient head (not shown), e.g., at a location $H_p$, a large robotic drive system 2, an imaging or optics cart 3, a medical instruments or sterile tools table 4, e.g., for carrying sterile medical tools, a guide user cart 5, ultrasound equipment 6, monitoring equipment 7, a Nico® Myriad® system 8, a Mayo® stand 9, a guide monitor 10 for navigation and optics, a navigation camera 11, a patch board 12, e.g., for connecting power, Ethernet, gas, and the like. Also, medical personnel 15 may include physicians, surgeons, e.g., a surgeon 16, surgical assistants, e.g., a surgical assistant 17, ultrasound technicians, anesthesiologists, nurses, residents, interns, scrub technicians, e.g., a scrub technician 18, and the like, by example only. Typically, a related art MRI machine (not shown) is large and cumbersome. Related art MRI machines are typically not used in the operating room OR, but related art MRI machines are used to obtain preoperative scans in another area of a hospital (not shown). In addition, related art MRI machines are incompatible with a large robotic drive system 2. As such, intraoperative MRI images are not available when a medical procedure uses the large robotic drive system 2.

These related art MRI systems and robotic systems have experienced many challenges, such as an absence of any integrated solution for systematic treatment of stroke and other neurological diseases and an inability to implement a related art MRI system, being large in size, in relation to other medical systems, e.g., robotic systems, unless disposed outside the related art MRI system's magnetic field. Accordingly, a need exists, in the related art, for apparatuses and methods that optimize floorspace in a medical environment, such as an operating theater and that are compatible with a robotic system in the medical environment.

SUMMARY

In addressing at least many of the challenges experienced in the related art, the present disclosure involves an MRI system and methods for use with a medical robotic system, e.g., a surgical, robotic system, in a medical, clinical, or surgical environment. The MRI system and methods of the present disclosure are also particularly useful in relation to a robotic system comprising a robotic apparatus, wherein the robotic apparatus comprises a C-arm. For example, a robotic apparatus comprises an interventional robotic apparatus, an Auris™ robotic apparatus, and a CT robotic apparatus.

In accordance with an embodiment of the present disclosure, an MRI system for use with a medical robotic system comprises an MRI apparatus configured to operate with the surgical robotic system, the MRI apparatus comprising at least one low-field magnet, the at least one low-field magnet configured to generate a low magnetic field, and the low magnetic field comprising a magnetic flux density in a range of approximately 0.1 Tesla (T) to approximately 0.5 T, whereby a standoff between the MRI apparatus and the surgical robotic system is reduced.

In accordance with another embodiment of the present disclosure, a method of providing an MRI system for use with a surgical robotic system comprises providing an MRI apparatus configured to operate with the surgical robotic system, providing the MRI apparatus comprising providing at least one low-field magnet, providing the at least one low-field magnet comprising configuring the at least one low-field magnet to generate a low magnetic field, and configuring the at least one low-field magnet to generate a low magnetic field with a magnetic flux density in a range of approximately 0.1 T to approximately 0.5 T, whereby a standoff between the MRI apparatus and the surgical robotic system is reduced.

In accordance with yet another embodiment of the present disclosure, a method of using an MRI system with a surgical robotic system comprises providing an MRI apparatus configured to operate with the surgical robotic system, providing the MRI apparatus comprising providing at least one low-field magnet, providing the at least one low-field magnet comprising configuring the at least one low-field magnet to generate a low magnetic field, and configuring the at least one low-field magnet to generate a low magnetic field with a magnetic flux density in a range of approximately 0.1 T to approximately 0.5 T, providing the MRI apparatus comprises configuring the MRI apparatus to operate with the surgical robotic system comprising an interventional robotic apparatus, and providing the MRI apparatus comprises configuring the MRI apparatus to operate with the surgical robotic system comprising a robotic apparatus having at least one of a C-arm and an optional fluoro-table; and disposing the MRI apparatus in relation to at least one of the C-arm and the fluoro-table of the robotic apparatus, an x-ray imaging apparatus, and a patient, thereby reducing a standoff between the MRI apparatus and the surgical robotic system.

Some of the features in the present disclosure are broadly outlined in order that the section, entitled Detailed Description, is better understood and that the present contribution to the art by the present disclosure is better appreciated. Additional features of the present disclosure are described hereinafter. In this respect, understood is that the present disclosure is not limited in its implementation to the details of the components or steps as set forth herein or as illustrated in the several figures of the Drawing, but are capable of being carried out in various ways which are also encompassed by the present disclosure. Also, understood is that the phraseology and terminology employed herein are for illustrative purposes in the description and are not regarded as limiting.

BRIEF DESCRIPTION OF THE DRAWING

The above, and other, aspects, and features, of the several embodiments in the present disclosure will be more apparent from this disclosure as presented in conjunction with the following several figures of the Drawing.

Figure 1:
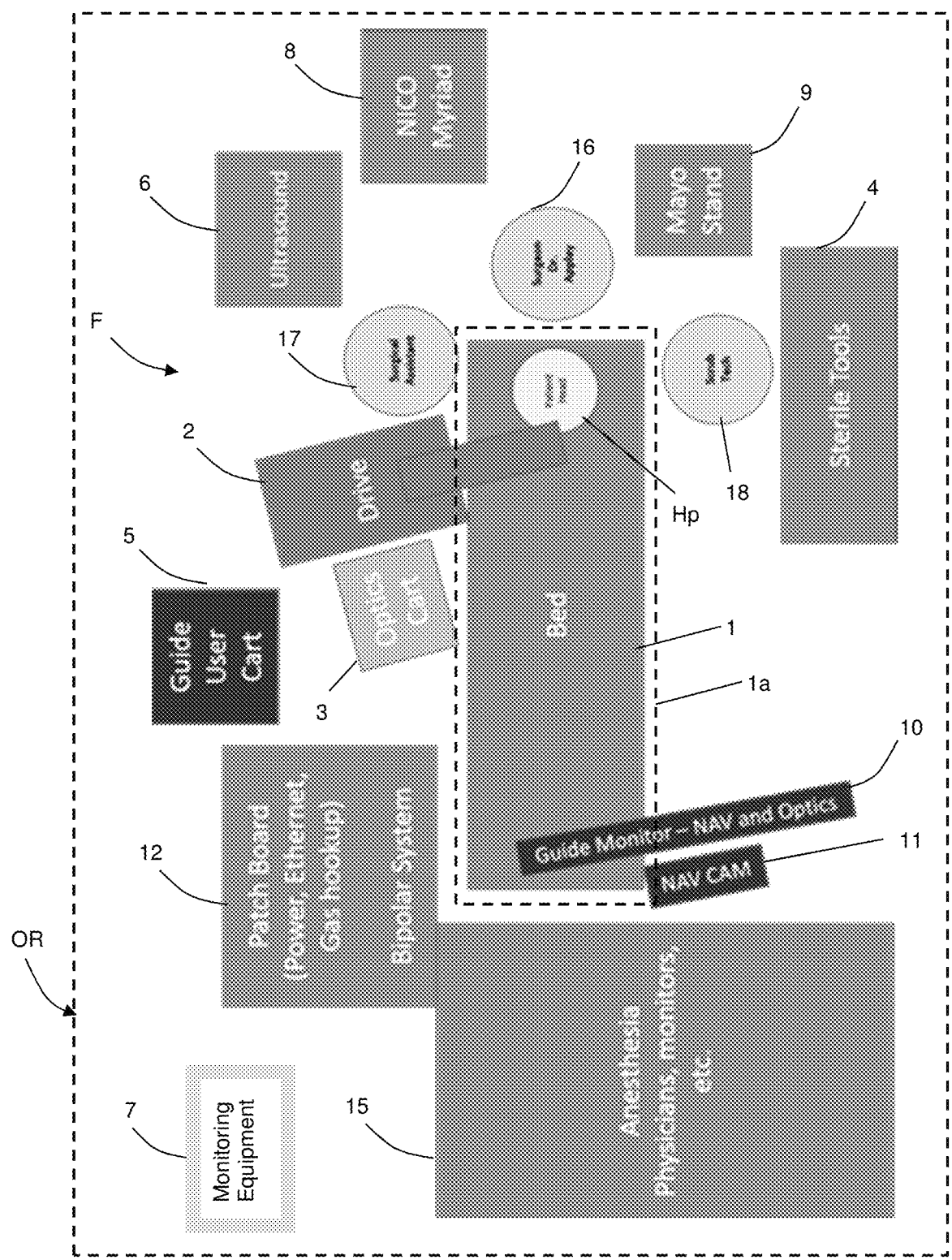
FIG. 1 is a diagram illustrating the limited useable floorspace in an operating theater, such as an operating room, which results in many challenges for medical personnel, in accordance with the prior art.

Corresponding reference numerals or characters indicate corresponding components throughout the several figures of the Drawing. Elements in the several figures are illustrated for simplicity and clarity and have not necessarily been drawn to scale. For example, the dimensions of some elements in the figures are emphasized relative to other elements for facilitating understanding of the various presently disclosed embodiments. Also, well-understood elements that are useful or necessary in commercially feasible embodiment are often not depicted to facilitate a less obstructed view of these various embodiments of the present disclosure.

DETAILED DESCRIPTION

The systems and methods described herein are useful in the field of imaging and tracking, such as used in relation to neurosurgery, including oncological care, neurodegenerative disease, stroke, brain trauma, and orthopedic surgery. The subject matter of the present disclosure is applicable to imaging and tracking in relation to other conditions or fields of medicine. Noted is that, while the present disclosure describes examples in the context of imaging and tracking in relation to neurosurgery, the subject matter of the present disclosure is applicable to other surgical procedures that may use any type of imaging.

Various example apparatuses or processes are below-described. No below-described example embodiment limits any claimed embodiment; and any claimed embodiments may cover processes, products of manufacture, compositions of matter, devices, systems, or apparatuses that differ from those examples described below. The claimed embodiments are not limited to apparatuses or processes having all the features of any one of the processes, products of manufacture, compositions of matter, devices, systems, or apparatuses below-described or to features common to multiple or all the processes, products of manufacture, compositions of matter, devices, systems, or apparatuses below-described. The claimed embodiments optionally comprise any of the below described processes, products of manufacture, compositions of matter, devices, systems, or apparatuses.

Furthermore, numerous specific details are set forth in order to provide a thorough understanding of the disclosure. However, understood is that the embodiments described herein are practiced without these specific details. In other instances, well-known methods, procedures and components have not been described in detail so as not to obscure the embodiments described herein.

As used herein, the terms, "comprises" and "comprising" are to be construed as being inclusive and open ended, and not exclusive. Specifically, when used in the specification and claims, the terms, "comprises" and "comprising" and variations thereof denote the specified features, steps, or components that are included. These terms are not to be interpreted to exclude the presence of other features, steps or components.

As used herein, the term "exemplary" or "example" denotes "serving as an example, instance, or illustration," and should not be construed as preferred or advantageous over other configurations disclosed herein.

As used herein, the terms "about," "approximately," and "substantially" are intended to cover variations that may exist in the upper and lower limits of the ranges of values, such as variations in properties, parameters, and dimensions. In one non-limiting example, the terms "about," "approximately," and "substantially" are understood to denote plus or minus 20 percent or less than a described value.

Unless defined otherwise, all technical and scientific terms used herein are intended to have the same meaning as understood by one of ordinary skill in the art. Unless otherwise indicated, such as through context, as used herein, the following technical and scientific terms are intended to have the meanings as understood by one of ordinary skill in the art.

Figure 2:
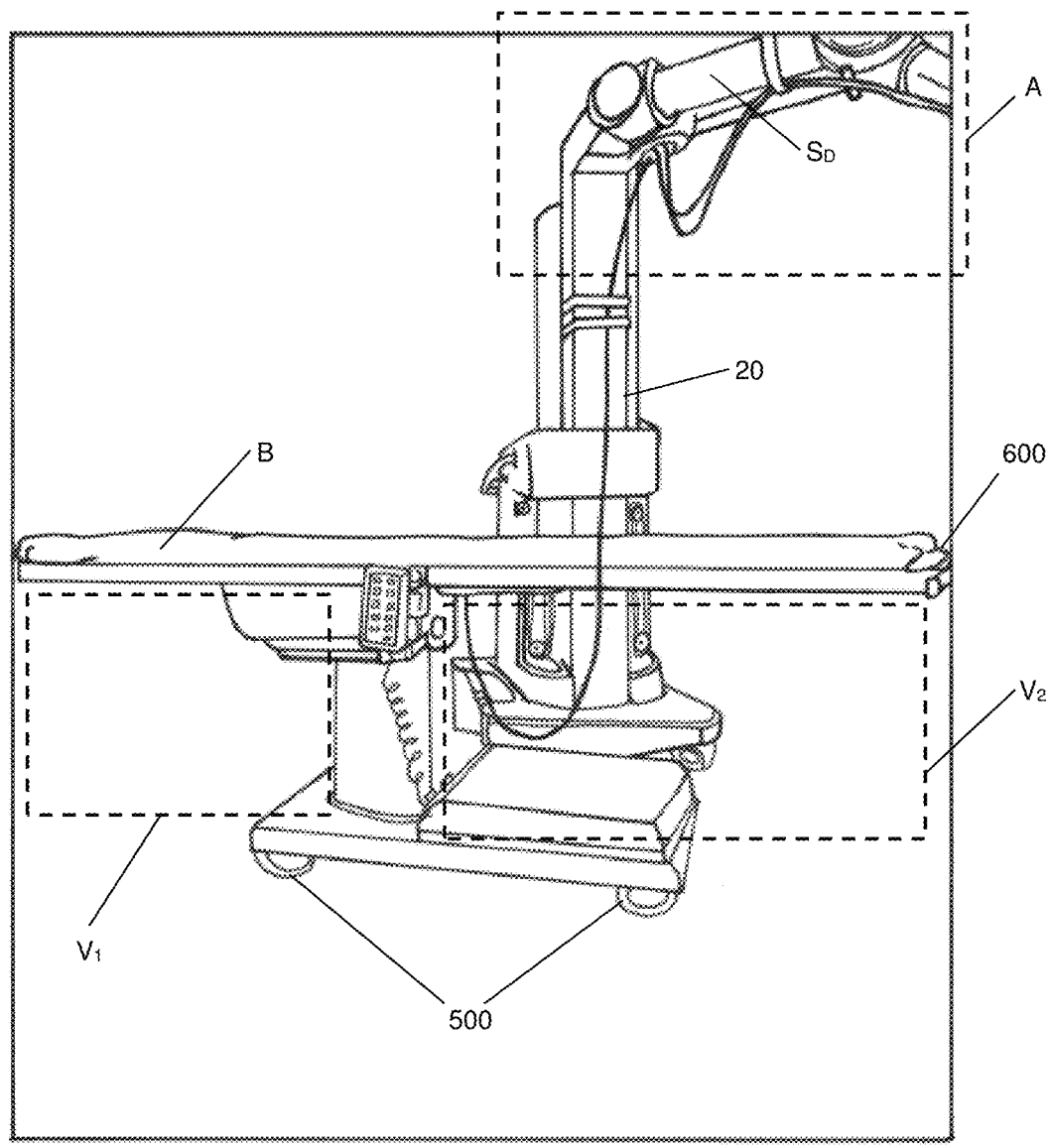
FIG. 2 is a diagram illustrating a perspective view of a robotic apparatus, as included in a drive system, wherein the robotic apparatus further comprises a motorized feature for automatically transporting the medical bed, in accordance with an embodiment of the present disclosure.

Referring to FIG. 2, this diagram illustrates, in a perspective view, a robotic apparatus A, as included in a drive system $S_D$, wherein a robotic apparatus A comprises further components (not shown) that are disposable in relation to the medical bed B, e.g., in relation to volumes $V_1$ and $V_2$, wherein the robotic apparatus A further comprises features, such as in relation to a support column 20 thereof, for coupling the drive system $S_D$ with the medical bed B, and wherein the robotic apparatus A further comprises a motorized feature 500 for automatically transporting the medical bed B, e.g., from a hospital room to the OR, by example only, in accordance with an embodiment of the present disclosure.

Figure 3:
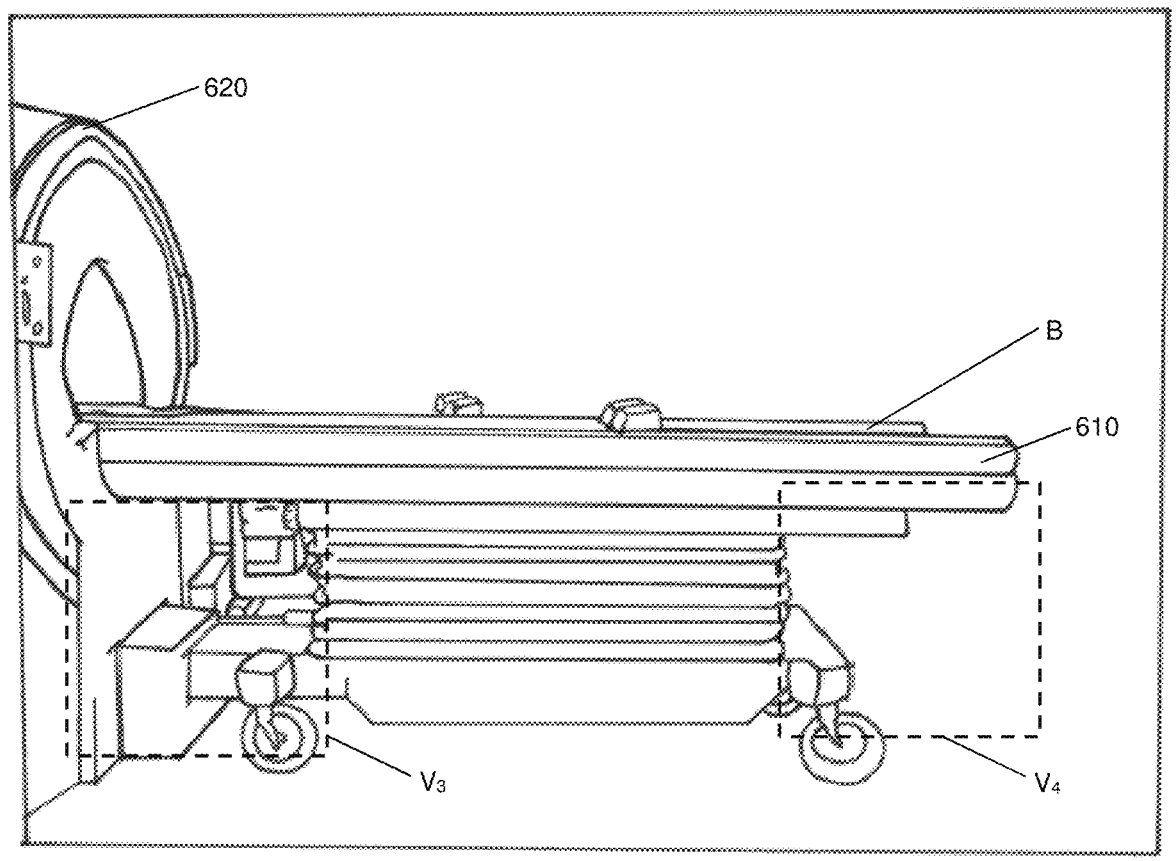
FIG. 3 is a diagram illustrating a perspective view of a medical bed, wherein a robotic apparatus therefor is disposable thereunder, the robotic apparatus operable in relation to magnetic resonance imaging (MRI) procedures by way of an MRI machine, in accordance with an embodiment of the present disclosure.

Referring to FIG. 3, this diagram illustrates, in a perspective view, a medical bed B, wherein a robotic apparatus A (FIG. 2) therefor is disposable in relation to the medical bed B, e.g., in relation to volumes $V_3$ and $V_4$, the robotic apparatus A operable in relation to magnetic resonance imaging (MRI) procedures an MRI machine 620, by example only, wherein the robotic apparatus A optionally further comprises a motorized feature 500 (FIG. 2) for automatically transporting the medical bed B, and wherein the robotic apparatus A further comprises a docking feature 600 (FIG. 2) for automatically docking, locking, undocking, and undocking the medical bed B, comprising an MRI table 610, with an imaging system, such as the MRI machine 620, by example only, in accordance with an embodiment of the present disclosure.

Figure 4:
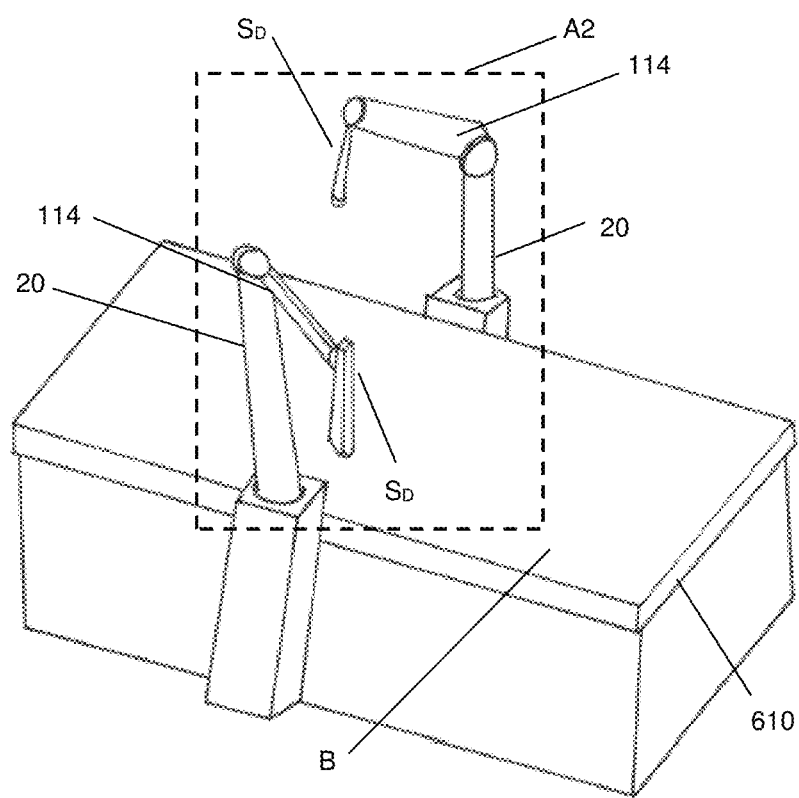
FIG. 4 is a diagram illustrating, in a perspective view, a robotic apparatus comprising a pair of robotic arms, e.g., as included in a drive system, in accordance with an embodiment of the present disclosure.

Referring to FIG. 4, this diagram illustrates, in a perspective view, a robotic apparatus A2 comprising pair of robotic arms 114, wherein each robotic arm 114 comprises further components, such as lighting devices, central processing units (CPUs), video equipment, and other hardware (not shown), that are disposable under the medical bed B, in accordance with an embodiment of the present disclosure. The apparatus A2 further comprises features, such as coupling features configured to couple the support column 20 of the drive system $S_D$ with the medical bed B. The robotic apparatus A2 further comprises a motorized feature 500 (FIG. 2) for automatically transporting the medical bed B. The robotic apparatus A2 further comprises a docking feature 600 (FIG. 2) for automatically docking, locking, unlocking, and undocking the medical bed B, comprising an MRI table 610, with an imaging system, such as an MRI machine 620 (FIG. 3), by example only. The apparatus A2 further comprises a motor and a rail system comprising a rail-and-slide assembly (not shown), wherein the slide element (not shown) of the rail-and-slide assembly is motorized for effecting translation of the apparatus A2 along a length of the medical bed B.

Figure 5:
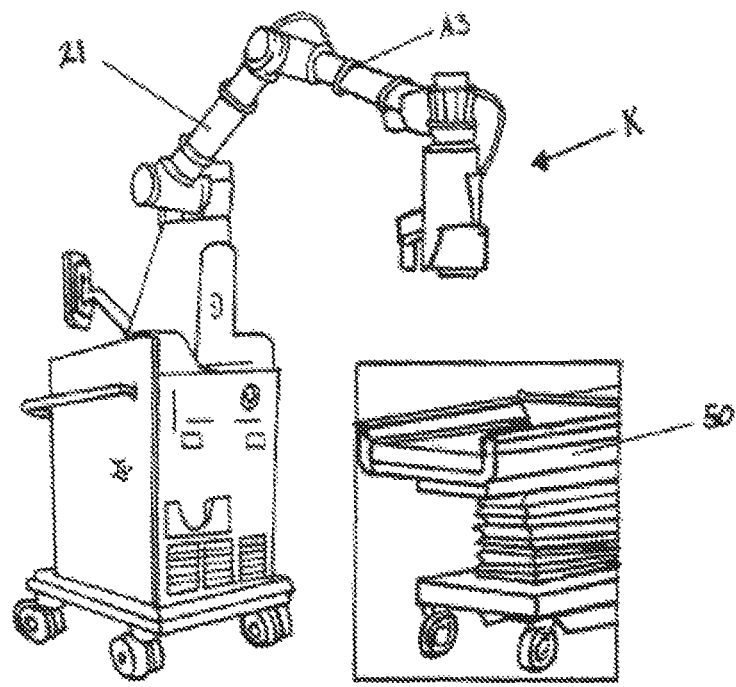
FIG. 5 is a diagram illustrating, in a perspective view, a robotic apparatus comprising a robotic arm, in accordance with an embodiment of the present disclosure.

Referring to FIG. 5, this diagram illustrates, in a perspective view, a robotic system K, comprising a robotic apparatus A3, the robotic apparatus A3 comprising a robotic arm 21, the at least one robotic arm 21 comprising at least one arm, and the robotic apparatus A3 optionally comprising a fluoro-table 50, in accordance with an embodiment of the present disclosure.

Figure 6:
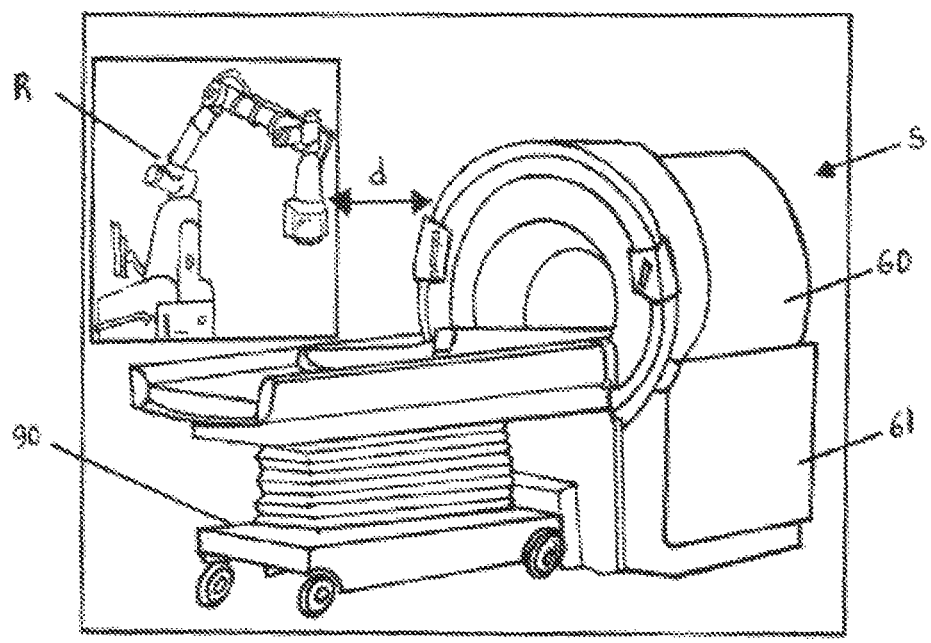
FIG. 6 is a diagram illustrating, in a perspective view, an MRI system for use with a medical robotic system, e.g., as shown in FIGS. 2-5, in accordance with an embodiment of the present disclosure.

Referring to FIG. 6, this diagram illustrates a magnetic resonance imaging (MRI) system S for use with a robotic system, the MRI system S comprising: an MRI apparatus 60 configured to operate with the robotic system 10 configured to generate a low magnetic field $B_L$, and the low magnetic field $B_L$ comprising a magnetic flux density in a range of approximately 0.1 T to approximately 0.5 T, whereby a standoff d between the MRI apparatus 60 and the robotic system R is reduced, in accordance with an embodiment of the present disclosure. By example only, the robotic system R comprises at least one of: a medical robotic system, a clinical robotic system, a diagnostic robotic system, and a surgical robotic system.

Still referring to FIG. 6, the MRI apparatus 60 is configured to at least one of: operate with the robotic system R comprising an interventional robotic apparatus A3; operate with the robotic system R comprising a robotic apparatus A3, the robotic apparatus A3 comprising at least one robotic arm 21, the at least one robotic arm 21 comprising at least one C-arm 40, and the robotic apparatus 20 optionally comprising a fluoro-table 50; and operate with the robotic system R comprising a robotic apparatus A3 having at least one of a metallic robotic device (not shown) and a metallic robotic tool (not shown) if the MRI system S operates outside the range of magnetic flux density for the low magnetic field $B_L$, in accordance with an embodiment of the present disclosure.

Still referring to FIG. 6, the MRI apparatus 60 comprises a footprint 61 in a range of approximately 250 square feet area, and wherein the standoff d comprises a distance in a range of approximately 0.1 meters (m) to approximately 1.0 m. Preferably, the footprint 61 comprises an area in a range of approximately 200 square foot area to 800 square foot area. Also, the robotic apparatus A3 is configured to at least one of: couple with a foot table 90; and integrate with the MRI apparatus 60, wherein the MRI apparatus 60 comprises an MRI coil 100.

Figure 7:
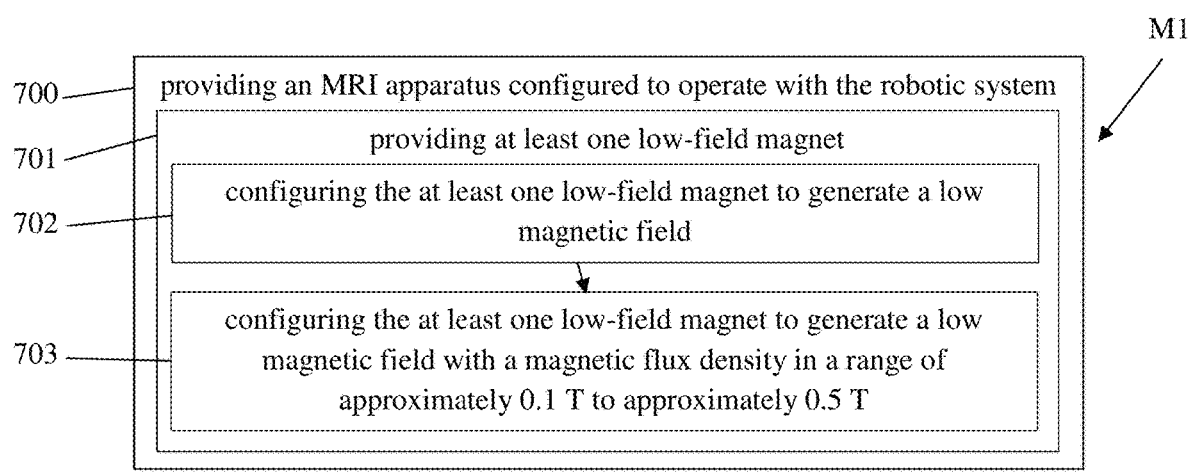
FIG. 7 is a flow diagram illustrating a method of providing an MRI system for use with a surgical robotic system, in accordance with an embodiment of the present disclosure.

Referring to FIG. 7, this flow diagram illustrates a method M1 of providing an MRI system S for use with a robotic system R, the method comprising: providing an MRI apparatus 60 configured to operate with the robotic system R, as indicated by block 700, providing the MRI apparatus 60 comprising providing at least one low-field magnet (not shown), as indicated by block 701, providing the at least one low-field magnet comprising configuring the at least one low-field magnet to generate a low magnetic field $B_L$, as indicated by block 702, and configuring the at least one low-field magnet to generate a low magnetic field $B_L$ with a magnetic flux density in a range of approximately 0.1 T to approximately 0.5 T, as indicated by block 703, whereby a standoff d between the MRI apparatus 60 and the robotic system R is reduced, in accordance with another embodiment of the present disclosure. By example only, providing the MRI apparatus 60 configured to operate with the robotic system R, as indicated by block 700, comprises providing the MRI apparatus 60 configured to operate with the robotic system R comprising at least one of: a medical robotic system, a clinical robotic system, a diagnostic robotic system, and a surgical robotic system.

Still referring to FIG. 7, in the method M1, providing the MRI apparatus 60, as indicated by block 700, comprises configuring the MRI apparatus 60 to at least one of: operate with the robotic system R comprising an interventional robotic apparatus A3; operate with the robotic system R comprising the interventional robotic apparatus A3, the robotic apparatus A3 comprising at least one robotic arm 21, the at least one robotic arm 21 comprising at least one C-arm 40, and the robotic apparatus A3 optionally comprising a fluoro-table 50; and operate with the robotic system R comprising the interventional robotic apparatus 20 having at least one of a metallic robotic device and a metallic robotic tool if the MRI system S operates outside the range of magnetic flux density for the low magnetic field $B_L$.

Still referring to FIG. 7, in the method M1, providing the MRI apparatus 60, as indicated by block 700, comprises at least one of: configuring the MRI apparatus 60 as portable and disposable adjacent the interventional robotic apparatus A3 in a surgical environment; and configuring the MRI apparatus 60 with a footprint 61 comprising an area in a range of approximately 250 square foot ($ft^2$), and wherein the standoff d comprises a distance in a range of approximately 0.1 m to approximately 1.0 m. Preferably, in the method M1, the footprint 61 comprises an area in a range of approximately 200 $ft^2$ area to approximately 800 $ft^2$, and the standoff d comprises a distance in a range of approximately 0.1 m to approximately 1.0 m. Also, in the method M1, the robotic apparatus A3 configured to at least one of: couple with a foot table 90 (FIG. 6); and integrate with the MRI apparatus 60, wherein the MRI apparatus 60 comprises an MRI coil (not shown).

Figure 8A:
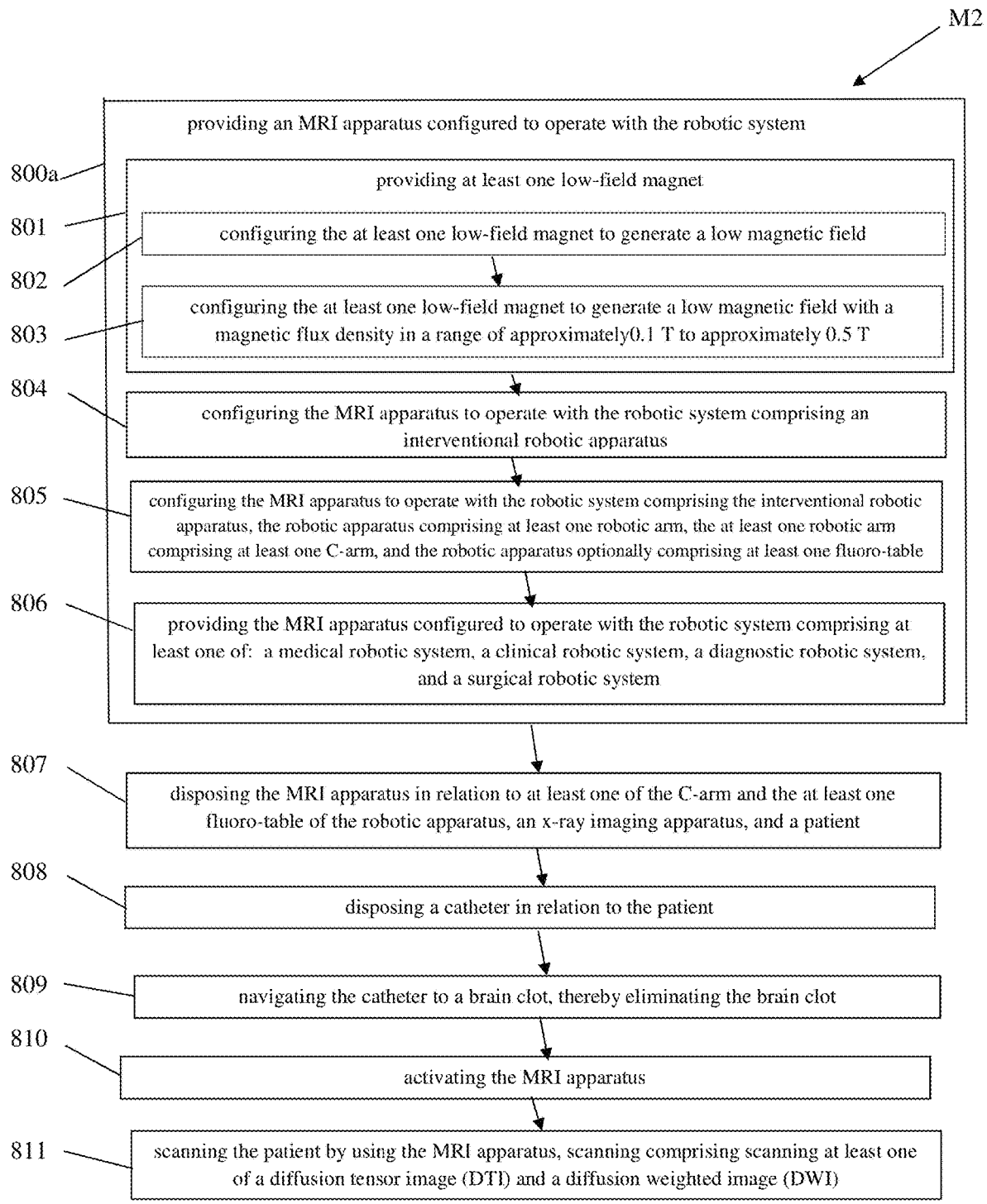
FIG. 8A is a flow diagram illustrating a method of using an MRI system with a surgical robotic system, in accordance with an embodiment of the present disclosure.

Referring to FIG. 8A, this flow diagram illustrates a method M2 of using an MRI system S with a robotic system R, by example only, comprising: providing an MRI apparatus 60 configured to operate with the robotic system S, as indicated by block 800a, providing the MRI apparatus 60 comprising providing at least one low-field magnet (not shown), as indicated by block 801, providing the at least one low-field magnet comprising configuring the at least one low-field magnet to generate a low magnetic field as indicated by block 802, and configuring the at least one low-field magnet to generate a low magnetic field $B_L$ with a magnetic flux density in a range of approximately 0.1 T to approximately 0.5 T, as indicated by block 803, providing the MRI apparatus 60 comprises configuring the MRI apparatus A to operate with the robotic system R comprising an interventional robotic apparatus A3, as indicated by block 804, and providing the MRI apparatus 60 comprises configuring the MRI apparatus 60 to operate with the robotic system comprising the interventional robotic apparatus A3, the robotic apparatus A3 comprising at least one robotic arm 21, the at least one robotic arm 21 comprising at least one C-arm 40, and the robotic apparatus 20 optionally comprising a fluoro-table 50, as indicated by block 805; and disposing the MRI apparatus 60 in relation to at least one of the C-arm 40 and the fluoro-table 50 of the robotic apparatus 20, an x-ray imaging apparatus X, and a patient P, as indicated by block 807, thereby reducing a standoff d between the MRI apparatus 60 and the robotic system S, in accordance with yet another embodiment of the present disclosure. By example only, providing the MRI apparatus 60 configured to operate with the robotic system R, as indicated by block 800, comprises providing the MRI apparatus 60 configured to operate with the robotic system R comprising at least one of: a medical robotic system, a clinical robotic system, a diagnostic robotic system, and a surgical robotic system, as indicated by block 806.

Still referring to FIG. 8A, the method M2 further comprises: disposing a catheter (not shown) in relation to the patient (not shown), as indicated by block 808; navigating the catheter to a brain clot (not shown), thereby eliminating the brain clot, as indicated by block 809; activating the MRI apparatus 60, as indicated by block 810; and scanning the patient by using the MRI apparatus 60, scanning comprising scanning at least one of a diffusion tensor image (DTI) and a diffusion weighted image (DWI) as indicated by block 811, thereby providing an MRI scan (not shown).

Figure 8B:
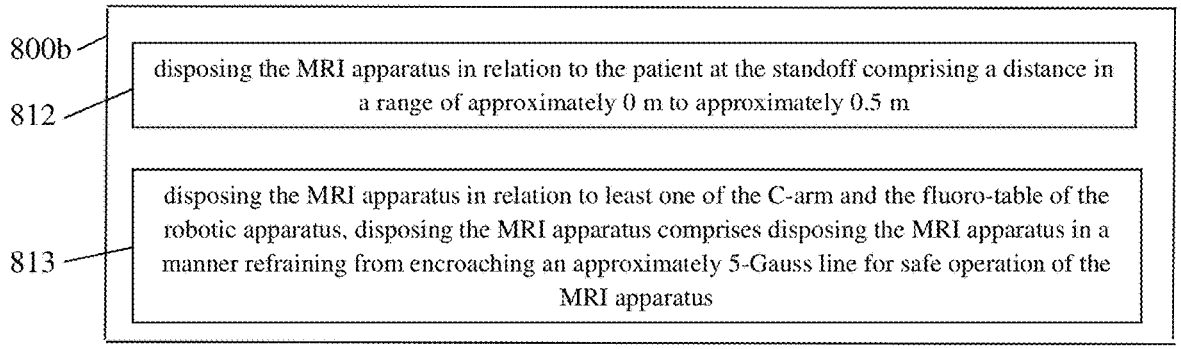
FIG. 8B is a flow diagram illustrating the method of using an MRI system with a surgical robotic system, as shown in FIG. 8A, further comprising optional steps, in accordance with an embodiment of the present disclosure.
Figure 8C:
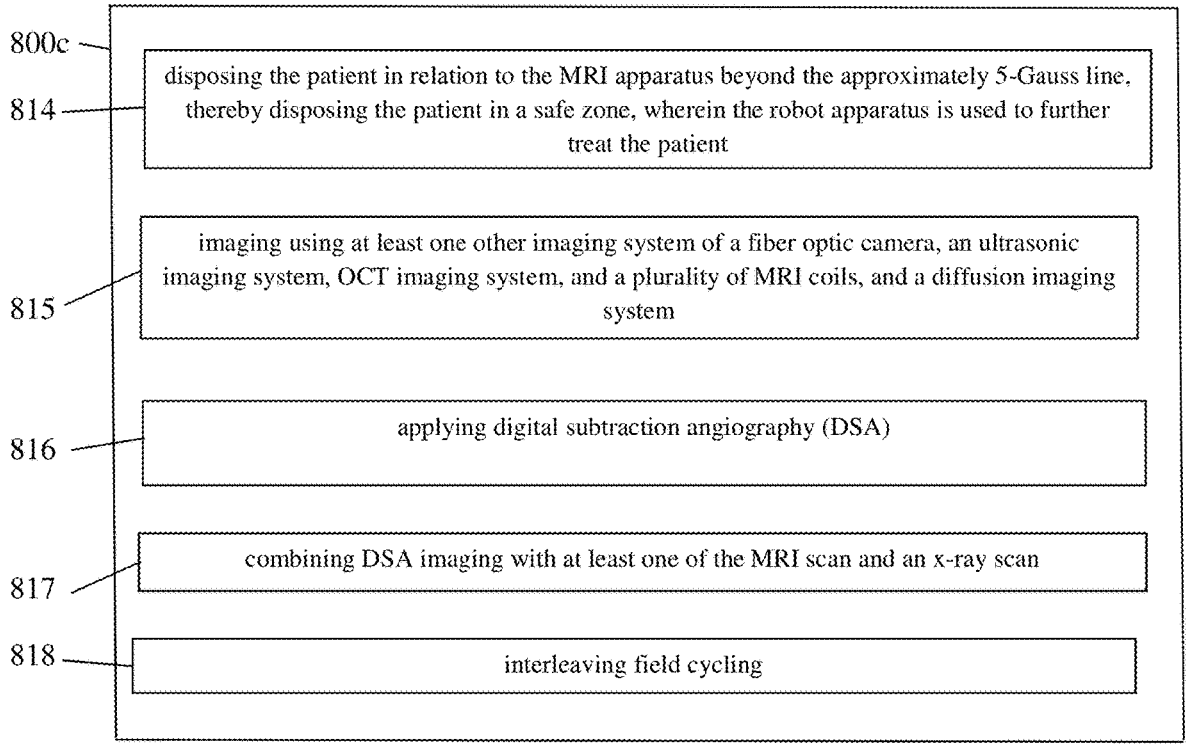
FIG. 8C is a flow diagram illustrating the method of using an MRI system with a surgical robotic system, as shown in FIGS. 8A and 8B, further comprising optional steps, in accordance with an embodiment of the present disclosure.

Referring to FIG. 8B, this flow diagram illustrates the method of using the MRI system S with the surgical robotic system R, as shown in FIG. 8A, further comprising optional steps, as indicated by block 800b, in accordance with an embodiment of the present disclosure. By example only, the method M2 further comprises at least one of: disposing the MRI apparatus 60 in relation to the patient (not shown) at the standoff d comprising a distance in a range of approximately 0 m to approximately 0.5 m, as indicated by block 812; and disposing the MRI apparatus 60 in relation to least one of the C-arm 40 and the fluoro-table 50 of the robotic apparatus A3, disposing the MRI apparatus 60 comprises disposing the MRI apparatus 60 in a manner refraining from encroaching an approximately 5-Gauss line for safe operation of the MRI apparatus, as indicated by block 813.

Referring to FIG. 8B, this flow diagram illustrates the method of using the method of using the MRI system S with the surgical robotic system R, as shown in FIGS. 8A and 8B, further comprising optional steps, in accordance with an embodiment of the present disclosure. By example only, the method M2, further comprises at least one optional step, as indicated by block 800c, of: disposing the patient (not shown) in relation to the MRI apparatus 60 beyond the approximately 5-Gauss line, thereby disposing the patient in a safe zone (not shown), wherein the robot apparatus A3 is used to further treat the patient, as indicated by block 814; imaging using at least one other imaging system (not shown) of a fiber optic camera, an ultrasonic imaging system, OCT imaging system, and a plurality of MRI coils, and a diffusion imaging system, as indicated by block 815; applying digital subtraction angiography (DSA) (not shown), as indicated by block 816; combining DSA imaging with at least one of the MRI scan and an x-ray scan, as indicated by block 817; and interleaving field cycling, as indicated by block 818.

At least some aspects disclosed are embodied, at least in part, in software. That is, some disclosed techniques and methods are carried out in a computer system or other data processing system in response to its processor, such as a microprocessor, executing sequences of instructions contained in a memory, such as ROM, volatile RAM, non-volatile memory, cache or a remote storage device.

A computer readable storage medium is used to store software and data which when executed by a data processing system causes the system to perform various methods or techniques of the present disclosure. The executable software and data is stored in various places including for example ROM, volatile RAM, non-volatile memory and/or cache. Portions of this software and/or data are stored in any one of these storage devices.

Examples of computer-readable storage media may include, but are not limited to, recordable and non-recordable type media such as volatile and non-volatile memory devices, read only memory (ROM), random access memory (RAM), flash memory devices, floppy and other removable disks, magnetic disk storage media, optical storage media, e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium is the internet cloud, or a computer readable storage medium such as a disc.

Furthermore, at least some of the methods described herein are capable of being distributed in a computer program product comprising a computer readable medium that bears computer usable instructions for execution by one or more processors, to perform aspects of the methods described. The medium is provided in various forms such as, but not limited to, one or more diskettes, compact disks, tapes, chips, universal server bus (USB) keys, external hard drives, wire-line transmissions, satellite transmissions, internet transmissions or downloads, magnetic and electronic storage media, digital and analog signals, and the like. The computer usable instructions may also be in various forms, including compiled and non-compiled code.

At least some of the elements of the systems described herein are implemented by software, or a combination of software and hardware. Elements of the system that are implemented via software are written in a high-level programming language such as object-oriented programming or a scripting language. Accordingly, the program code is written in C, C++, J++, or any other suitable programming language and may comprise functions, modules or classes, as is known to those skilled in computer programming. At least some of the elements of the system that are implemented via software are written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner for performing at least one of the methods described herein.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, any particular order to steps or stages of methods or processes described in this disclosure is not intended or implied. In many cases the order of process steps is varied without changing the purpose, effect, or import of the methods described.

Information as herein shown and described in detail is fully capable of attaining the above-described embodiments of the present disclosure and the presently preferred embodiment, if any, of the present disclosure, and is, thus, representative of the subject matter which is broadly contemplated by the present disclosure. The scope of the present disclosure fully encompasses other embodiments and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims.

Moreover, no requirement exists for a device, an apparatus, a system, or a method to address each, and every, problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail is made, without departing from the spirit and scope of the present disclosure, as set forth in the appended claims, as is apparent, or may become apparent, to those of ordinary skill in the art, are also encompassed by the present disclosure.

INDUSTRIAL APPLICABILITY

Generally, the present disclosure applies to MRI technologies. More particularly, the present disclosure applies to MRI and robotic technologies. Even more particularly, the present disclosure applies to MRI and robotic technologies for surgical implementations.

What is claimed:

1. A magnetic resonance imaging (MRI) system for use with a surgical robotic system, the MRI system comprising:
an MRI apparatus configured to operate with the surgical robotic system, the MRI apparatus comprising at least one low-field magnet, the at least one low-field magnet configured to generate a low magnetic field, and the low magnetic field comprising a magnetic flux density in a range of approximately 0.1 T to approximately 0.5 T,
wherein a standoff between the MRI apparatus and the surgical robotic system;
wherein the MRI apparatus is configured to operate with the surgical robotic system comprising an interventional robotic apparatus having a C-arm or an imaging system;
wherein the MRI apparatus is configured to operate with the surgical robotic system comprising an interventional robotic apparatus having at least one of a metallic robotic device and a metallic robotic tool during the MRI system operating outside the range of magnetic flux density for the low magnetic field;
wherein the metallic robotic tool is disposable adjacent the surgical robotic system in a surgical environment;
wherein the MRI apparatus is configured to scan a patient using a diffusion weighted image (DWI) MRI scan;
wherein the MRI apparatus in relation to at least one of the C-arm and the imaging system of the interventional robotic apparatus is configured for refraining from encroaching a 5-Gauss line for safe operation of the MRI apparatus;
wherein the MRI apparatus is configured to interleave scanning the patient using the MRI apparatus with field cycling;
wherein the imaging system of the interventional robotic apparatus further comprises a fiber optic camera to facilitate interventional imaging disposed within a catheter; and
wherein the catheter is configured to navigate a brain clot in the brain of the patient;
wherein the MRI apparatus is configured to generate a first set of DWI images of the patient and the imaging system of the interventional robotic apparatus is configured to generate a secondary set images of the patient.

2. The MRI system of claim 1, wherein the MRI apparatus comprises a footprint in an area range of approximately 200 ft² to approximately 800 ft², and wherein the standoff comprises a distance in a range of approximately 0.1 m to approximately 1 m.

3. The MRI system of claim 1, wherein the surgical robotic system is configured to be at least one of:
coupled with a foot table; and
integrate with the MRI apparatus, wherein the MRI apparatus comprises an MRI coil.

4. A method of using an MRI system with a surgical robotic system, the method comprising:

providing an MRI apparatus configured to operate with the surgical robotic system, providing the MRI apparatus comprising providing at least one low-field magnet, providing the at least one low-field magnet comprising configuring the at least one low-field magnet to generate a low magnetic field, and configuring the at least one low-field magnet to generate a low magnetic field with a magnetic flux density in a range of approximately 0.1 T to approximately 0.5 T,
providing the MRI apparatus comprises configuring the MRI apparatus to operate with the surgical robotic system comprising an interventional robotic apparatus,
providing the MRI apparatus comprises configuring the MRI apparatus to operate with the surgical robotic system comprising an interventional robotic apparatus having a C-arm or an imaging system; and
disposing the MRI apparatus in relation to at least one of the C-arm and the interventional robotic apparatus, an x-ray imaging apparatus, and a patient,
thereby reducing a standoff between the MRI apparatus and the surgical robotic system;
disposing a catheter in relation to the patient;
navigating the catheter to a brain clot, thereby eliminating the brain clot;
activating the MRI apparatus;
scanning the patient by using the MRI apparatus, scanning comprising scanning a diffusion weighted image (DWI), thereby providing an MRI scan;
interleave scanning the patient using the MRI apparatus with field cycling;
wherein disposing the MRI apparatus in relation to at least one of the C-arm and the imaging system of the robotic apparatus configured for refraining from encroaching a 5-Gauss line for safe operation of the MRI apparatus;
wherein the imaging system of the interventional robotic apparatus further comprises a fiber optic camera to facilitate interventional imaging disposed within the catheter; and
wherein the MRI apparatus is configured to generate a first set of DWI images of the patient and the imaging system of the interventional robotic apparatus is configured to generate a secondary set images of the patient.

5. The method of claim 4, wherein providing the MRI apparatus comprises configuring the MRI apparatus with a footprint in an area range of approximately 200 ft² to approximately 800 ft², and wherein the standoff comprises a distance in a range of approximately 0.1 m to approximately 1.0 m.

6. The method of claim 4, wherein disposing the MRI apparatus in relation to the patient comprises disposing the MRI apparatus in relation to the patient in the standoff comprising a distance in a range of approximately 0.1 m to approximately 1.0 m.

7. The method of claim 4, wherein, if the MRI scan indicates a surgical complication, disposing the patient in relation to the MRI beyond the 5-Gauss line, thereby disposing the patient in a safe zone, and wherein the robot apparatus is used to further treat the patient.

8. The method of claim 4, further comprising imaging using at least one other imaging system of an ultrasonic imaging system, OCT imaging system, a plurality of MRI coils, and a diffusion imaging system.

9. The method of claim 4, further comprising at least one of:
applying digital subtraction angiography (DSA); and combining DSA imaging with at least one of the MRI scan and an x-ray scan; and interleaving field cycling.

10. The MRI system claim 1, wherein the imaging system of the interventional robotic apparatus is further selected from a list to facilitate interventional imaging consisting of an ultrasonic imaging system, an OCT imaging system, a plurality of MRI coils, and a diffusion imaging system.

11. The method of claim 1, wherein interleave scanning the patient using the MRI apparatus with field cycling further comprises using a delta relaxation enhanced magnetic resonance (DREMR) field-cycled imaging MRI technique.

\* \* \* \* \*